US00PP12475P2

(12) United States Plant Patent
Kaskel

(10) Patent No.: US PP12,475 P2
(45) Date of Patent: Mar. 19, 2002

(54) HEMEROCALLIS PLANT NAMED 'FIRST SPRING'

(75) Inventor: Matthew Kaskel, Miami, FL (US)

(73) Assignee: Twyford Plant Laboratories, Inc., Sebring, FL (US)

( * ) Notice: Subject to any disclaimer, the term of this patent is extended or adjusted under 35 U.S.C. 154(b) by 0 days.

(21) Appl. No.: 09/564,461

(22) Filed: May 3, 2000

(51) Int. Cl.[7] ..... A01H 5/00
(52) U.S. Cl. ..... Plt./263

(58) Field of Search ..... Plt./263

*Primary Examiner*—Bruce R. Campell
*Assistant Examiner*—Anne Marie Grünberg
(74) *Attorney, Agent, or Firm*—Foley & Lardner

(57) ABSTRACT

A new and distinct cultivar of Hemerocallis plant named 'First Spring' characterized by its peach colored flowers with a red eye zone and picotee edge which are borne on short branched scapes. Plants of 'First Spring' bloom early and repeatedly throughout the growing season. Plants of 'First Spring' are evergreen and clump-forming, thus they are attractive in landscapes. The plant grows vigorously and propagated easily by division or tissue culture.

2 Drawing Sheets

BACKGROUND OF THE INVENTION

The present invention comprises a new and distinct cultivar of Hemerocallis plant, hereinafter referred to by the cultivar name 'First Spring'. The genus Hemerocallis is a member of the family Liliaceae.

Hemerocallis comprises a genus of approximately 15 species of clump-forming, herbaceous perennials which are native to central Europe, China, and particularly, Japan. The flowers of Hemerocallis are lily-like and are borne in succession atop tall, frequently-branched scapes. Individual flowers last one day; thus, Hermerocallis is commonly know as 'Daylily' in commercial trade.

In recent years, Hemerocallis has been extensively hybridized, and many cultivars exist. Hermerocallis hybrids are hardy spring- and summer-blooming plants which are particularly well-adapted to landscape plantings.

The plants form clumps of fan-shaped crowns of vertically-ranked, keeled, strap-like leaves. Plants (individual crowns) range in size from approximately 20 cm to over 90 cm in spread. Depending upon the parentage, Hemerocallis hybrids may be deciduous, evergreen or semi-evergreen.

Hemerocallis hybrids come in a range of colors including orange, yellow, pink, reddish or purplish. The flowers are funnel-shaped or campanulate with six segments joined at the base into a tube.

Asexual propagation of Hemerocallis if frequently done by division. Propagation can also be done through the use of tissue culture practices.

The new cultivar 'First Spring' is a product of a planned breeding program and was originated by the inventor, Matthew Kaskel, from a cross made during such a program in Homestead, Fla. in April of 1994. The male and female parents are proprietary Hemerocallis selections designated by number codes which are maintained by the inventor and used for breeding purposes only. The selection comprising the new variety was chosen after commencement of flowering of the progeny in April of 1995.

Asexual reproduction of the new cultivar by tissue culture and division was performed by the inventor in Homestead, Fla. and has demonstrated that the combination of characteristics as herein disclosed for new cultivar 'First Spring' are firmly fixed and are retained through successive generations of asexual reproduction.

BRIEF DESCRIPTION OF THE INVENTION

The following traits have been repeatedly observed and are determined to be basic characteristics of 'First Spring' which in combination distinguish this Hemerocallis as a new and distinct cultivar:

1. Flowers having three zones of color, which include peach with a red eye zone, a picotee margin and a yellow center;

2. Individual scapes which are short and branched with many buds which open in succession for approximately 4 weeks;

3. Spent flowers shrivel, become inconspicuous, drop from the scape quickly, and do not interfere with the opening of subsequent flowers;

4. Plants begin blooming early in the season and rebloom throughout a 90-day blooming season;

5. Plants grow vigorously and propagate rapidly by division and tissue culture; and 6. Plants have evergreen foliage and a clumping habit making them attractive in landscapes even when not in bloom.

'First Spring' has not been observed under all possible environmental conditions. The phenotype of the new cultivar may significantly with variations in environment such as temperature, light intensity, day length and humidity, without any change in genotype.

BRIEF DESCRIPTION OF THE DRAWINGS

The accompanying color photographic illustrations show typical characteristics of Hemerocallis 'First Spring', with colors being as nearly true as possible with illustrations of this type.

The first drawing shows a 10-month-old plant of 'First Spring' grown from tissue culture and flowering in a landscape setting.

The second drawing is a close-up view showing the characteristics of the flowers and scape.

DETAILED BOTANICAL DESCRIPTION

The following observations, measurements and values describe plants grown in Sebring, Fla., under landscape conditions which closely approximate those generally used in horticultural practice. Color references are made to The Royal Horticultural Society (R.H.S.) Colour Chart, except where general color terms of ordinary significance are used.

Classification:

*Commercial.*—Hemerocallis cv. 'First Spring'.

Parentage:

*Male parent.*—Proprietary selection of Hemerocallis.

*Female parent.*—Proprietary selection of Hemerocallis.

Propagation: Vegetative, by tissue culture or division.

Plant:

*Form growth habit.*—Clump-forming; fan-shaped crowns of vertically ranked, opposite, smooth, keeled, ligulate leaves.

*Height.*—Approximately 50 cm to 55 cm including inflorescence.

*Width.*—Approximately 60 cm to 65 cm.

Foliage:

*Size.*—Mature leaves are approximately 50 cm to 60 cm long and 2.0 cm to 3.5 cm wide (flattened).

*Shape.*—The leaf blade is ligulate with an acute tip. The margins are entire. The leaves are curved over their length. The leaf is keeled with the tip slightly twisted and curved downward.

*Surface texture.*—The leaf blade is relatively thin with a smooth surface.

*Color.*—Upper and lower surfaces are medium-green, RHS 137B–C.

*Average number.*—Approximately 8–10 pairs.

*Dormancy.*—Plants are evergreen and require no dormant period. If grown in appropriate conditions, plants are capable of growing year-round.

Inflorescence:

*Borne.*—Flowers are borne in succession with new buds opening daily atop a 4- to 6-branched scape. Scapes may produce approximately 23–30 buds with each branch having 4–7 buds.

*Shape.*—Short, alternately-branched scape.

*Buds.*—Dimensions: Approximately 7.2 cm to 8.5 cm long and 2.5 cm wide Color: Basically green; becoming yellower than, but closest to, RHS 163D before opening.

*Individual flowers.*—Number of sepals: three. Number of petals: three. Dimension: The diameter of the flower is approximately 12.5 cm to 13 cm. The sepals are approximately 7.6 cm long and approximately 3.5 cm wide. The petals are approximately 7.5 cm long and approximately 5.5 cm wide. Shape: Funnel-form to campanulate, segments ovate and moderately reflexed. Petals are distinctly wavy along the margins. Sepals are slightly wavy along the margins. Color: Upper Surface: Sepals and petals are orange, RHS 24C–D; eye zone and picotee margin are RHS 182A–D; throat is yellow, RHS 9A, tinged with green; eye zone coloration pronounced on petals and faint on sepals. Sepal patterns are the same as the petals but are less intense and less vivid. Sepal tips are tingled with green. Petal mid-veins are very faintly tinged with greyed-red RHS 182D, surrounded by yellow-orange RHS 19D. Sepals typically do not have reddish picotee margins. Lower surface: Sepals and petals are orange, RHS 24C–D; throat is yellow, RHS 24D, tinged with green; sepals tipped with RHS 146D. Texture: Moderately thick; leathery. Quantity: Approximately 23–30 flowers/buds present depending on the size of the plant and inflorescence. Branch spikes contain approximately 4 to 7 flowers/buds.

*Senescent flower.*—Spent flowers collapse and shrivel, becoming inconspicuous, eventually falling from the scape in 1 or 2 days.

*Scape.*—Approximately 45 cm to 50 cm in height and 11 mm in diameter measured at the midpoint, RHS 146A.

*Bracts.*—Small leaf-like bracts are present at the junctions of the branches and the scape and also the flower buds and the scape. The bracts are variable in size with the largest being approximately 12.5 cm and the smallest being approximately 1.0 cm in length; approximately 3.0 cm to 4.5 cm in width, RHS 146B.

*Time of blooming.*—In mature plants, flowering begins approximately early in the spring (mid-March as observed in Sebring, Fla.).

*Duration of blooms.*—Individual flowers last 1 day, and the total duration of flowering is about 90 days with subsequent scapes appearing throughout the season.

*Fragrance.*—Slight.

Reproductive organs:

*Ovary.*—Superior, oblong, 5 mm long and 5 mm wide, RHS 145A.

*Pistil.*—8.9 cm long and 2.0 mm wide, RHS 26D.

*Stamens.*—Six present; filament is flat and approximately 3.4 cm–4.2 cm long and 2 mm–3 mm wide, RHS 163D.

*Anthers.*—6 mm long, black to brown in color.

*Pollen.*—RHS 23A.

Seed characteristics: Not observed.

Roots: Very thick, fleshy, white roots with fine laterals.

Cultural:

*USDA Zone.*—Grows and blooms best when grown in USDA Zones 6 to 11.

Diseases/pests: No unusual susceptibilities. Aphids may infest plants during winter months.

I claim:

1. A new and distinct cultivar of Hemerocallis plant named 'First Spring' as illustrated and described.

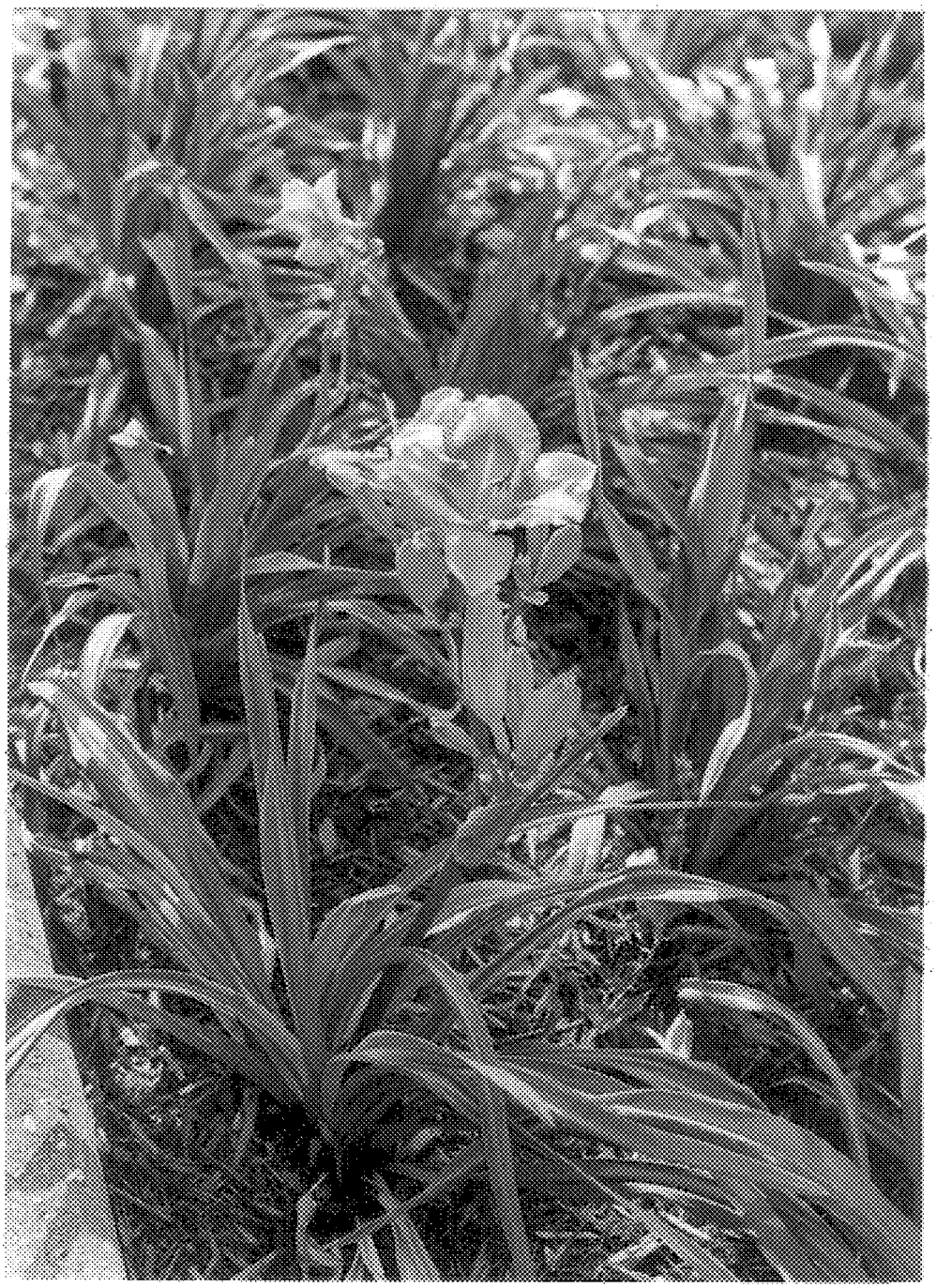

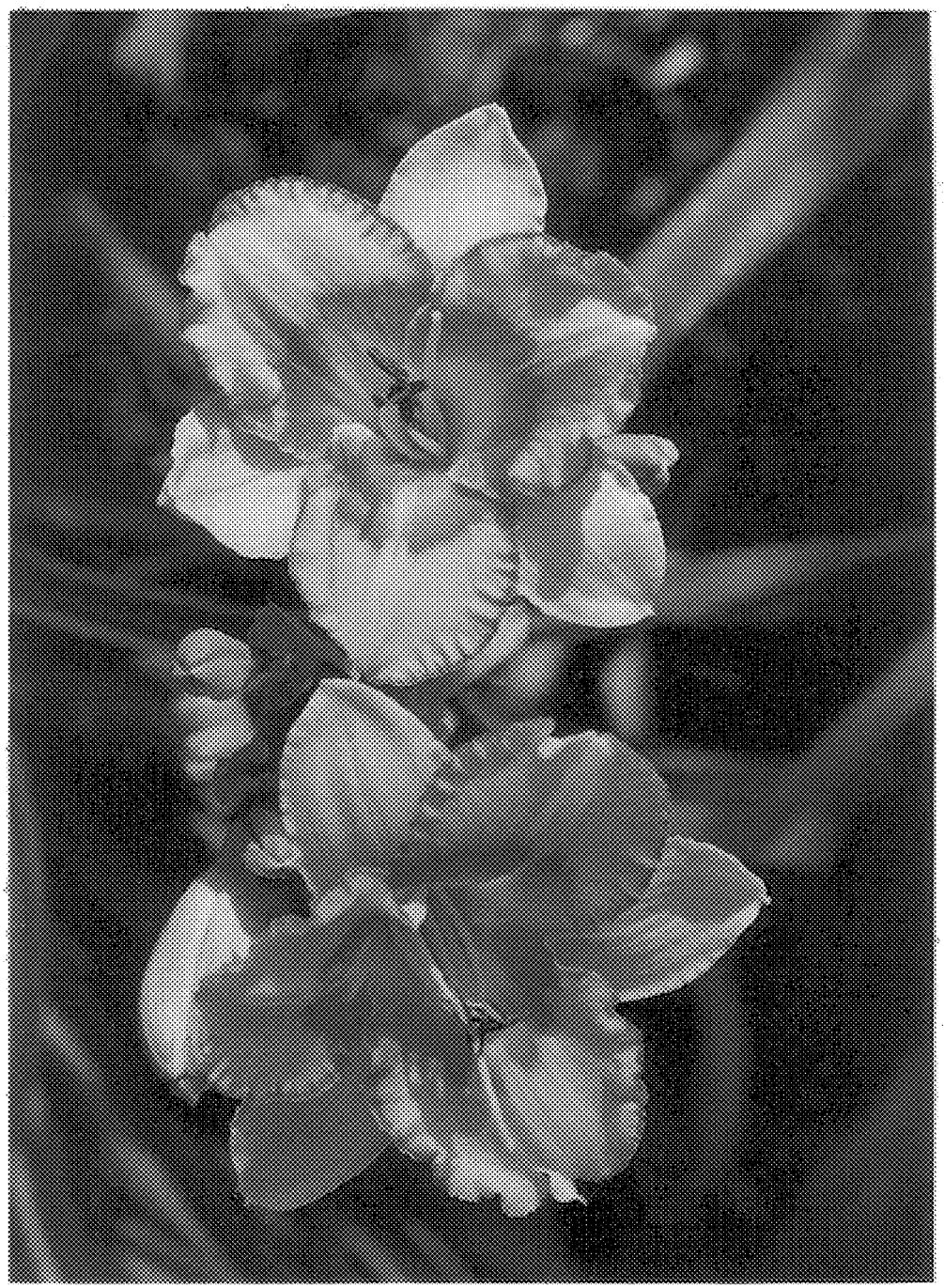

* * * * *